（12）United States Patent
Sibilio et al.

(10) Patent No.: US 11,220,553 B2
(45) Date of Patent: Jan. 11, 2022

(54) ERBB2-TARGETING ANTIBODY

(71) Applicant: ISTITUTO BIOCHIMICO ITALIANO GIOVANNI LORENZINI S.P.A., Aprilia (IT)

(72) Inventors: Leonardo Sibilio, Rome (IT); Patrizio Giacomini, Rome (IT)

(73) Assignee: ISTITUTO BIOCHIMICO ITALIANO GIOVANNI LORENZINI S.P.A., Aprilia (IT)

( * ) Notice: Subject to any disclaimer, the term of this patent is extended or adjusted under 35 U.S.C. 154(b) by 64 days.

(21) Appl. No.: 16/090,505

(22) PCT Filed: Mar. 31, 2017

(86) PCT No.: PCT/EP2017/057697
§ 371 (c)(1),
(2) Date: Oct. 1, 2018

(87) PCT Pub. No.: WO2017/167967
PCT Pub. Date: Oct. 5, 2017

(65) Prior Publication Data
US 2019/0112387 A1    Apr. 18, 2019

(30) Foreign Application Priority Data
Apr. 1, 2016  (IT) .......................... 102016000033776

(51) Int. Cl.
| *C07K 16/32* | (2006.01) |
| *A61K 39/395* | (2006.01) |
| *G01N 33/574* | (2006.01) |
| *A61K 47/68* | (2017.01) |
| *A61P 35/00* | (2006.01) |
| *A61K 31/282* | (2006.01) |
| *A61K 39/00* | (2006.01) |

(52) U.S. Cl.
CPC ............ *C07K 16/32* (2013.01); *A61K 31/282* (2013.01); *A61K 47/6803* (2017.08); *A61P 35/00* (2018.01); A61K 2039/505 (2013.01); A61K 2039/507 (2013.01); C07K 2317/24 (2013.01); C07K 2317/30 (2013.01); C07K 2317/73 (2013.01)

(58) Field of Classification Search
CPC combination set(s) only.
See application file for complete search history.

(56) References Cited

FOREIGN PATENT DOCUMENTS

| WO | 2011/147982 A2 | 12/2011 |
| WO | 2013/164689 A2 | 11/2013 |
| WO | 2015/130173 A1 | 9/2015 |
| WO | 2015/195917 A1 | 12/2015 |

OTHER PUBLICATIONS

Pedersen et al (Molecular Cancer Therapeutics, 2015, 14:669-680).*
International Search Report and Written Opinion for corresponding Application No. PCT/EP2017/057697 (dated Jun. 6, 2017).
Meng et al., "A Monoclonal Antibody Targeting ErbB2Domain III Inhibits ErbB2 Signaling and Suppresses the Growth of ErbB2—Overexpressing Breast Tumors," Oncogen. 5(3):e211 (2016).
Rockberg et al., "Discovery of Epitopes for Targeting the Human Epidermal Growth Factor Receptor 2 (HER2) with Antibodies," Mol. Oncol. 3(3):238-247 (2009).
De Marco, "Methodologies for the Isolation of Alternative Binders with Improved Clinical Potentiality over Conventional Antibodies," Crit. Rev. Biotechnol. 33(1):40-48 (2013).

* cited by examiner

*Primary Examiner* — Laura B Goddard
(74) *Attorney, Agent, or Firm* — Troutman Pepper Hamilton Sanders LLP (Rochester)

(57) ABSTRACT

The present invention relates to an antibody, particularly a monoclonal antibody, which binds a novel epitope of the ERBB2 tyrosine kinase receptor, wherein the unique features of said binding enable interference with receptor-mediated signalling and downstream biological effects in a novel and unanticipated fashion not obtainable with state-of-the-art therapeutic antibodies. The present invention relates to compositions comprising such an antibody and its humanized derivative, as well as methods using such an antibody and derivative, particularly in ERBB2-low/non-amplified breast cancers, particularly in combination with Trastuzumab and Pertuzumab.

19 Claims, 5 Drawing Sheets
Specification includes a Sequence Listing.

ERBB2-TARGETING ANTIBODY

This application is a national stage application under 35 U.S.C. § 371 of PCT Application No. PCT/EP2017/057697, filed 31 Mar. 2017, which claims priority of Italy Application No. 102016000033776, filed 1 Apr. 2016, which are hereby incorporated by reference in their entirety.

FIELD OF THE INVENTION

The present invention relates to the field of antibodies, particularly an antibody which binds a novel epitope of the ERBB2 tyrosine kinase.

STATE OF THE ART

Cancer is a generic term collectively defining the rapid proliferation of transformed cells that grow locally and/or invade and/or spread (metastases) to distant organs. Cancer is a leading cause of death worldwide, most of which due to metastases, breast cancer being the $5^{th}$ big killer.

An abnormal response to growth factors plays a major role in the natural history of human tumors. The ERBB family of receptor tyrosine kinases (RTK) includes four members (from the epidermal growth factor receptor ERBB1 or HER-1 through ERBB-4 or HER-4) signaling upon engagement in combinatorial dimeric receptor combinations. ERBB2 (also referred to as HER2 or Neu-Erb) is the shared (and preferred) heterodimerization partner, and the master coordinator and integrator of signaling amplification. Aberrant ERBB signaling is causally involved in the pathogenesis of human tumors including astrocytomas, head and neck squamous cell carcinomas, breast, ovary and prostate cancers, as well as melanoma and sarcoma. ERBB2 overexpression, most often caused by gene amplification, can be detected by immunohistochemistry in approximately 30% of breast carcinomas, is associated with an aggressive clinical course, and predictive of a worse prognosis. When engaged by several natural growth factors, including Neuregulin (NRG1), also called Heregulin (HRG), ERB RTK receptors become phosphorylated and trigger oncogenic intracellular signalling cascades, most notably the RAS-RAF-MAPK-ERK and PI3K-AKT pathways, involved in cell proliferation and cell survival, respectively. Antibodies to the ectodomain of the receptor molecule have provided, among other approaches, a very successful strategy to target the ERBB2 pathway. Therapeutic antibodies such as the prototypic Trastuzumab (Herceptin®) and Pertuzumab (Omnitarg®) antibodies have revolutionized cancer treatment because unlike conventional antiblastic and chemotherapeutic agents they specifically target antigen structures with restricted distribution to malignant cells. Trastuzumab and Pertuzumab (hitherto TTZ and PTZ) are recombinant, humanized antibodies that alone and in combination with chemotherapy are now regularly included among the preferred therapeutic options for patients with ERBB2-overexpressing/ERBB2-amplified breast cancer. The combination of TTZ and PTZ is active and well tolerated in patients with metastatic HER2-positive breast cancer who had experienced progression during prior TTZ therapy (Baselga J, et al. J Clin Oncol 2010; 28:1138-44).

Unfortunately, TTZ is clinically effective only in patients bearing breast carcinoma lesions in which the ERBB2 proto-oncogene is overexpressed and/or amplified. To identify these patients, international good clinical practice guidelines prescribe the use of IVD-certified immunohistochemistry kits. Patients are eligible for TTZ therapy when staining either reaches a 3+ intensity (high, ring-like homogeneous staining), or is at least 2+(e.g. incomplete ring pattern and/or heterogeneity across different areas of the lesion), but in this latter case the gene must be amplified, as assessed by cytogenetic methods.

In contrast, all the other breast carcinoma patients (ERBB2 1+/2+; non-amplified), that are the vast majority (approximately 70%), cannot take advantage of antibody-mediated ERBB2 receptor blockade. Moreover, even ERBB2-high tumors at diagnosis may secondarily lose ERBB2 to escape therapeutic anti-ERBB2 pressure (Tortora J. Natl. Cancer Inst. 2011; 43:95-8), leading to an increase in the number of ineligible patients upon relapse/progression. It would be highly desirable to extend the applicative range of antibody therapy to at least some patients in this heterogeneous ERBB2-low group.

To this end, one may want to develop additional antibodies to ERBB2. These must have the ability to complement, and/or substitute, and/or synergize with, the available therapeutic antibodies, primarily TTZ and PTZ. Ideally, these novel antibodies should do so in both ERBB2-high and ERBB2-low settings, making it possible to exert additive effects on TTZ-sensitive tumors on the one hand, and overcome primary as well as secondary resistance to treatment due to low ERBB2 expression, on the other.

Although many monoclonal antibodies to ERBB2 have been described by several groups, their antineoplastic properties in vitro and in vivo have not been assessed in detail in most cases. For instance, Digiesi G. et al. (Hybridoma 1992, 11(4), 519-527) described the production and characterization of murine mAbs to the extracellular domain of oncogene GP185HER2. Lombardi A. et al (Protein Expr. Purif. 2005, 44(1) 10-15) and Galeffi P. et al. (J. Translational Medicine 2006, 4(39), 1-13) described the expression of a single-chain antibody to ErbB-2 in E. coli, plants and cell-free systems. The encoding DNA sequences, as well as the molecular, biochemical, biological, and antiproliferative properties, if any, of these IgGs are unknown.

The aim of the present invention is therefore to provide an antibody other than TTZ and PTZ, said antibody that could be used, alone or in combination with TTZ and PTZ, for the treatment of cancer, in particular to improve ERBB2 receptor blockade in both ERBB2-high/amplified and ERBB2-low/non-amplified breast cancer cells and mouse xenografts.

SUMMARY OF THE INVENTION

The inventors have identified, characterized, and humanized a unique, novel antibody that binds an epitope located in the extracellular domain of ErbB2. Of interest, this epitope is distinct from the epitopes recognized by TTZ and PTZ. The unique features of said binding enable additive/synergistic interference with receptor-mediated signaling and downstream biological effects in a novel and unanticipated fashion not obtainable with state-of-the-art therapeutic antibodies. The novel antibody is able to induce tumor regression in tumors expressing low ERBB2 levels in which TTZ is expected to have low clinical efficacy. In addition, the novel antibody synergizes with TTZ and PTZ by inducing tumor regression in an additive fashion in both ERBB2-overexpressing and ERBB2-low tumors.

Thus, subject matter of the present invention is an antibody or fragment thereof which binds a unique epitope of the ERBB2 receptor and comprises:

a) a Heavy chain Variable (VH) domain having at least 80% identity to the Complementary Determining Regions (CDRs, boldface underlined types) in SEQ ID NO:1 and b) a Light chain Variable (VL) domain having at least 80% identity to the Complementary Determining Regions (CDRs, boldface underlined types) in SEQ ID NO:2.

```
VH sequence
                                        (SEQ ID NO: 1)
QVQLVQSGAEVKKPGASVKISCKASGYTFSNYWIEWVRQAPGQGLEWMGE

ILPGSGSTNYNEKLKGRVTSTRDTSISTAYMELSRLRSDDTGVYYCARGG

GNYPYYFDYWGQGTTVTVSS

VL sequence
                                        (SEQ ID NO: 2)
DIQMTQSPSTLSASVGDRVTITCKASQDVGTAVAWYQQKPGKAPKLLIYW

ASTRHTGVPSRFSGSGSGTEFTLTISSLQPDDFADYFCQQYSSYRTFGAG

TKLEIK
```

Surprisingly the antibody of the invention has the ability to inhibit ERBB2-sustained tumor growth in vitro and in vivo in a synergistic way with both TTZ and PTZ and in tumors that are refractory to either or both TTZ and PTZ.

The antibody called mAb W6/800, which is subject matter of the present invention, is other than TTZ and PTZ. This antibody may be used, alone or in combination with TTZ and PTZ, for the treatment of cancer to improve ERBB2 receptor blockade in both ERBB2-high/amplified and ERBB2-low/non-amplified breast cancer cells and mouse xenografts.

DETAILED DESCRIPTION OF THE INVENTION

As used herein, "sequence identity" between two polypeptide sequences, indicates the percentage of amino acids that are identical between the sequences, preferably over the entire length of the amino acid sequences as encoded by the CDR sequences in SEQ ID NO: 1 and/or SEQ ID NO: 2. Preferred polypeptide sequences of the invention have a sequence identity of at least 80%, more preferably 85%, even more preferably 90, 93%, 95%, 96%, 97%, 98% or 99%. The term antibody includes "fragments" or "derivatives", which have at least one antigen binding site of the antibody and/or show the same biological activity. Further, the antibody of the invention preferably comprises at least one heavy immunoglobulin chain and at least one light immunoglobulin chain. An immunoglobulin chain comprises a variable domain and optionally a constant domain. A variable domain may comprise complementary determining regions (CDRs), e.g. a CDR1, CDR2 and/or CDR3 region, and framework regions. The antibody of the invention may be any antibody of natural and/or synthetic origin, e.g. an antibody of mammalian origin. Preferably, the constant domain—if present—is a human constant domain. The variable domain is preferably a mammalian variable domain, e.g. a humanized or a human variable domain.

Antibodies according to the invention may be polyclonal or monoclonal antibodies. Monoclonal antibodies are preferred. In particular antibodies of the present invention are preferably selected from the group consisting of recombinant antibodies, humanized or fully human antibodies, chimeric antibodies, multispecific antibodies, in particular bispecific antibodies, or fragments thereof.

Monoclonal antibodies may be produced by any suitable method such as that of Köhler and Milstein (Nature 1975; 256:495-7) or by recombinant DNA methods. Monoclonal antibodies may also be isolated from phage antibody libraries using techniques described in Clackson et al. (Nature 1991; 352:624-8).

Humanized forms of the antibodies may be generated according to the methods known in the art such as chimerization or CDR grafting. Alternative methods for the production of humanized antibodies are well known in the art and are described in, e.g., EP-A1 0 239 400 and WO 90/07861. Human antibodies can also be derived by in vitro methods. Suitable examples include but are not limited to phage display, yeast display, and the like.

According to the present invention, "chimeric antibody" relates to antibodies comprising polypeptides from different species, such as, for example, mouse and human. The production of chimeric antibodies is described, for example, in WO 89/09622.

Preferably the antibody of the invention is a recombinant monoclonal humanized antibody as above described, comprising a Heavy chain Variable (VH) domain and a Light chain Variable (VL) domain with at least 80% identity to the above described CDRs, wherein the rest of the amino acid sequence of the VH is at least 80% identical to SEQ ID NO:1 and the rest of the amino acid sequence of the VL is at least 80% identical SEQ ID NO: 2 or SEQ ID NO: 3.

Preferred polypeptide sequences of the invention have a sequence identity of at least 80%, more preferably 85%, even more preferably 90%, 93%, 95%, 96%, 97%, 98% or 99%.

```
VL sequence
                                        (SEQ ID NO: 3)
AIQLTQSPSSLSASVGDRVTITCKASQDVGTAVAWYQQKPGKAPKLLIYW

ASTRHTGVPSRFSGSGSGTDFTLTISSLQPEDFADYFCQQYSSYRTFGAG

TKLEIK
``` wherein CDRs are boldface underlined type.

According to a preferred embodiment the antibody or fragment thereof as above described comprises a Heavy chain Variable (VH) domain having 100% identity with SEQ ID NO:1 and a Light chain Variable (VL) domain having 100% identity with SEQ ID NO:2 or SEQ ID NO:3.

According to a preferred embodiment the antibody or fragment thereof may be a Fab fragment, a Fab' fragment, a F(ab') fragment, a Fv fragment, a diabody, a small modular immunopharmaceutical (SMIP), an affibody, an avimer, a nanobody, a domain antibody, or an ScFv.

"Avimer" relates to a multimeric binding protein or peptide engineered using, for example, in vitro exon shuffling and phage display. Multiple binding domains are linked, resulting in greater affinity and specificity compared to single epitope immunoglobin domains.

"Nanobody" or single domain antibody relates to an antibody fragment consisting of a single monomeric variable antibody domain.

"Affibody" molecules are small high affinity proteins being engineered to bind specifically to a large number of target proteins.

The antibody of the invention may be preferably of the IgG1, IgG2, IgG3, IgG4, IgM, IgA1, IgA2, IgAsec, IgD, and IgE antibody-type. It will be appreciated that antibodies that are generated need not initially possess such an isotype, but rather the antibody as generated can possess any isotype and that the antibody can be isotype-switched.

The antibodies or antibody fragments of the invention are optionally deimmunized for therapeutic purposes. It will be apparent to those skilled in the art that the antibodies of the invention can be further coupled to other moieties for, e.g., drug targeting and imaging applications. Such coupling may be conducted chemically after expression of the antibody or antigen to site of attachment or the coupling product may be engineered into the antibody or antigen of the invention at the DNA level.

Thus, for diagnostic purposes, the antibody or antibody fragment of the invention may be labelled, i.e. coupled to a labelling group. Suitable labels include radioactive labels, fluorescent labels, suitable dye groups, enzyme labels, chromogenes, chemiluminescent groups, biotinyl groups, predetermined polypeptide epitopes recognized by a secondary reporter etc.

Those labelled antibodies or antibody fragments may be in particular used in immunohistochemistry assays or for molecular imaging in vivo.

For therapeutic purposes, the antibody or antibody fragment of the invention may be conjugated with a effector group, in particular a therapeutic effector group such as a radioactive group or a cytotoxic group.

Labelling groups or effector groups may be attached by spacer arms of various lengths to reduce potential steric hindrance.

According to another aspect, the present invention relates to a nucleic acid molecule encoding the antibody of the invention or fragment thereof or a nucleic acid capable of hybridizing thereto under stringent conditions. The nucleic acid molecule of the invention encoding the above-described antibody, antibody fragment or derivative thereof may be, e.g. DNA, cDNA, RNA or synthetically produced DNA or RNA or recombinantly produced chimeric nucleic acid molecule comprising any of those nucleic acid molecules either alone or in combination. The nucleic acid molecule may also be genomic DNA corresponding to the entire gene or a substantial portion thereof or to fragments and derivatives thereof. In a particular preferred embodiment of the present invention, the nucleic acid molecule is a cDNA molecule.

The term "hybridizing under stringent conditions" means that two nucleic acid fragments hybridize with one another under standardized hybridization conditions as described for example in Sambrook et al., "Expression of cloned genes in *E. coli*" in Molecular Cloning: A laboratory manual (1989), Cold Spring Harbor Laboratory Press, New York, USA. Such conditions are for example hybridization in 6.0×SSC at about 45° C. followed by a washing step with 2.0×SSC at 50° C., preferably 2.0×SSC at 65° C., or 0.2×SSC at 50° C., preferably 0.2×SSC at 65° C.

Another aspect of the invention relates to a vector comprising a nucleic acid molecule of the invention. Said vector may be, for example, a phage, plasmid, viral or retroviral vector. Retroviral vectors may be replication competent or replication defective. Preferably, the vector of the invention is an expression vector wherein the nucleic acid molecule is operatively linked to one or more control sequences allowing the transcription and optionally expression in prokaryotic and/or eukaryotic host cells.

The invention further relates to a host comprising the vector of the invention. Said host may be a prokaryotic or eukaryotic cell or a non-human transgenic animal. The polynucleotide or vector of the invention which is present in the host may either be integrated into the genome of the host or it may be maintained extrachromosomally. The host can be any prokaryotic or eukaryotic cell, such as a bacterial, insect, fungal, plant, animal, mammalian or, preferably, human cell. Preferred fungal cells are, for example, those of the genus *Saccharomyces*, in particular those of the species *S. cerevisiae*.

The invention additionally relates to a method for the preparation of an antibody, comprising culturing the host of the invention under conditions that allow synthesis of said antibody and recovering said antibody from said culture.

A further aspect of the present invention relates to a pharmaceutical composition comprising the antibody of the invention or a fragment thereof, the nucleic acid molecule, the vector, the host of the invention or an antibody obtained by a method of the invention. The term "composition" as employed herein comprises at least one compound of the invention. Preferably, such a composition is a therapeutical/pharmaceutical or a diagnostic composition.

The diagnostic composition of the invention may be used for assessing the onset or the disease status of a hyperproliferative disease as defined herein.

The composition preferably comprises a pharmaceutically acceptable carrier, diluent and/or excipient.

Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers, excipients and/or diluents can be formulated by well known conventional methods.

Administration of the suitable compositions may be effected by different ways, e.g., by intravenous, intraperitoneal, subcutaneous, intramuscular, topical, intradermal, intranasal or intrabronchial administration. Preferred is an intravenous, intramuscular and/or subcutaneous administration.

These pharmaceutical compositions can be administered to the subject at a suitable dose. The dosage regimen can be determined by the attending physician and clinical factors.

The compositions of the invention may be administered locally or systemically. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents depending on the intended use of the pharmaceutical composition.

According to an especially preferred embodiment the composition comprises a further active agent, such as a further antibody or antibody fragment.

Preferably the antibody and the composition of the invention is for use in combination with at least one further antineoplastic agent. Said combination is effective, for example, in inhibiting abnormal cell growth. Many antineoplastic agents are presently known in the art. In general the term includes all agents that are capable of prevention, alleviation and/or treatment of hyperproliferative disorders. Especially preferred are antineoplastic agents inducing apoptosis.

Preferably the antineoplastic agent is selected from the group consisting of antibodies, small molecules, nanoparticles, antimetabolites, alkylating agents, topo-isomerase inhibitors, microtubule-targeting agents, kinase inhibitors, protein synthesis inhibitors, immuno-therapeutics, hormones or analogs thereof, DNA nanobinders, and/or mTOR inhibitors.

Specific examples of antineoplastic agents which can be used in combination with the antibodies provided herein include, for example, gefitinib, lapatinib, sunitinib, pemetrexed, bevacizumab, cetuximab, imatinib, alemtuzumab, trastuzumab, pertuzumab, rituximab, erlotinib, bortezomib and the like, in particular trastuzumab and pertuzumab. Other specific antineoplastic agents to be used in the compositions as described and claimed herein include for example, chemotherapeutic agents such as Paclitaxel, Anthracyclines, Fluoropirimidine, *vinca* alkaloids, platinum salts, in particular capecitabine, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, melphalan, cyclophosphamide, 6-mercaptopurine, 6-thioguanine, cytarabine (CA), 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin and diethylstilbestrol (DES).

The antibody and the compositions of the invention may be administered in combination with a further therapeutic composition comprising an active agent as described above and/or irradiation and/or radiotherapy.

According to a preferred embodiment, the compositions of the invention are for the use in treating and/or preventing hyperproliferative diseases, in particular neoplastic diseases or cancer. The compositions may also be used for the manufacture of a medicament for treating and/or preventing hyperproliferative diseases, in particular neoplastic diseases or cancer.

A hyperproliferative disease as defined herein includes any neoplasia, i.e. any abnormal and/or uncontrolled new growth of tissue. The term "uncontrolled new growth of tissue" as used herein may depend upon a dysfunction and/or loss of growth regulation. A hyperproliferative disease includes tumor diseases and/or cancer, such as metastatic or invasive cancers.

The hyperproliferative disease is preferably selected from disorders associated with, accompanied by or caused by ERBB2 expression, overexpression or hyperactivity, such as cancer, in particular melanoma, breast cancer, ovarian cancer, renal carcinoma, gastrointestinal/colon cancer, lung cancer, clear cell carcinoma of the kidney, prostate cancer and/or sarcomas. In particular, for these tumors, it has been demonstrated a role of ERBB2 in promoting cancer development and growth, and thus the inhibition of this protein could give certain benefits.

The invention further relates to a method of treating a disease wherein the antibody of the invention is administered to a mammal and wherein said disease is correlated directly or indirectly with an abnormal level of expression or activity of ERBB2, particularly but not exclusively when ERBB2 expression is low to intermediate upon IVD immunohistochemistry testing (e.g. 1+/2+ by IHC), and the ERBB2 gene is not amplified, making it inappropriate and clinically ineffective the administration of TTZ.

Yet another aspect of the present invention is directed to a method of diagnosing a cancer associated with ERBB2 in a subject, comprising
(a) contacting ex vivo or in vivo cells from the subject with an antibody or antigen binding portion thereof of any one of the preceding claims and
(b) measuring the level of binding to ERBB2 on the cells, wherein abnormally high levels of binding to ERBB2 indicate that the subject has a cancer associated with ERBB2.

In terms of the present invention, "abnormally high" means higher binding levels of ERBB2 compared to a healthy subject having no cancer.

Preferably the subject is an animal, more preferably a mammalian and in particular preferably a human.

EXPERIMENTAL SECTION

Production of mAb W6/800 from a Hybridoma Cell Line: General Procedures.

Materials and Methods:

4-week old BALB/c female mice were immunized for three times at weekly intervals by intraperitoneal injection of NIH/3T3 cells ($1 \times 10^7$) transfected with the human ERBB2 receptor. Five days following the last immunization, splenocytes were removed for somatic cell fusion (Köhler and Milstein, Nature 1975; 256:495-7) with the murine non-secreting myeloma cell line NS-1. Hybridomas secreting antibodies binding to transfectants, but not to the parental NIH/3T3 cells, were cloned twice by limiting dilution and were further characterized by flow cytometry, indirect immunoprecipitation, as well as binding on several ERBB2 transfectants but not parental cells and human cell lines known to lack ERBB2. Antibodies were further screened for their ability to inhibit the hyper-proliferative state of human breast carcinoma cell lines such as the ERBB2-amplified/overexpressing cell lines SKBR3 and BT-474, shown in previous studies to be electively sensitive to TTZ and PTZ (Baselga J, et al. J Clin Oncol 2010; 28:1138-44). From this preliminary screening, mAb W6/800 was thereby obtained, that suppresses the growth and $^3$H-thymidine incorporation in these cell lines. These results suggested that mAb W6/800 may be similar in its biological properties to TTZ and PTZ, and led to further studies and the unexpected findings exemplified below.

Example 1: Features of mAb W6/800

Materials and methods: mAb W6/800 is an IgG2a. Ig sequences SEQ ID NO: 4 and SEQ ID NO:5

(SEQ ID NO: 4)
QVQLQQSGAELMKPGASVKISCKATGYTFSNYWIEWVKQRPGHGLEWIGE

ILPGSGSTNYNEKLKGKATFTADTSSNTAYMQLSSLTSEDSGVYYCARGG

GNYPYYFDYWGQGTTVTVSS (SEQ ID NO: 5)
IELMTQSHKFMSTSVGDRVSITCKASQDVGTAVAWYQQKPGQSPKLLIYW

ASTRHTGVPDRFTGSGSGTDFTLTISNVQSEDLADYFCQQYSSYRTFGAG

Figure 1:
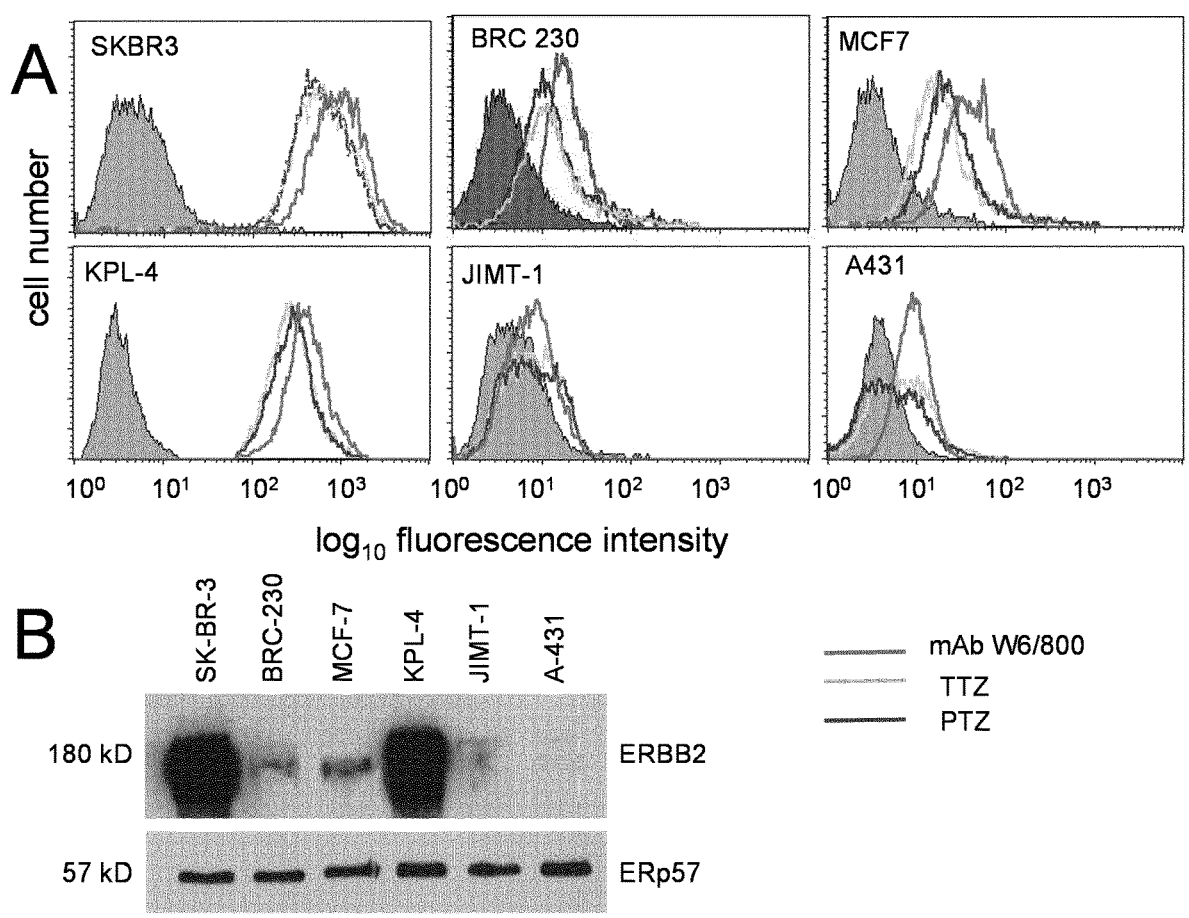
FIG. 1 compares mAb W6/800, TTZ and PTZ in their ability to bind breast carcinoma cells known to express different levels of ERBB2, from overexpression to undetectable expression.

TKLE were obtained by retro-transcription from hybridoma total cellular RNA and PCR amplification with degenerate primer pairs as described (Wang Z, et al. J Immunol Methods 2000; 233:167-77).

mAb W6/800 purified from hybridoma cultures, as well as TTZ and PTZ (obtained from commercial preparations for in vivo clinical use) were tested by flow cytometry for their ability to bind breast carcinoma cell lines expressing different levels of ERBB2 to determine whether binding patterns are similar or different (FIG. 1A). These breast carcinoma cells were also assessed by Western Blotting with a polyclonal antibody to ERBB2 (FIG. 1B). In FIG. 1A, target cells were incubated for 30 min with the three mAbs (10 μg/ml) in parallel, washed twice, and then incubated for 30 min with optimal pre-determined dilutions of Fluorescein IsoThioCyanate (FITC)-labeled secondary antibody to either mouse Ig (murine W6/800), or human Ig (humanized TTZ and PTZ), and read in a Becton & Dickinson FACScan flow cytometer. In FIG. 1B, nonionic detergent soluble extracts from the indicated, representative cell lines (100 μg/lane total cellular proteins) were resolved by SDS-PAGE and electroblotted onto a nitrocellulose filter. The filter was cut in two stripes, each of which was separately decorated with mAb 3D5 to ERBB2 (Thermo Scientific) and a polyclonal antibody to ERp57 (produced in-house), as an equalization control.

Results:

TTZ, PTZ and mAb W6/800 bind all the tested cell lines. The relative levels of ERBB2 expression in the different cells are concordantly estimated by the three mAbs by flow cytometry (FIG. 1A), and are consistent with the levels independently assessed by a fourth distinct antibody in Western Blotting (FIG. 1B). Internal negative controls are included in which the primary antibody is a murine IgG2 of irrelevant specificity. These are shown as grey shaded histograms (FIG. 1A). Only background staining with murine Igs is shown, since the signal with a control human Ig is superimposable. Thus, mAb W6/800 appears to be similar, under certain respects, to TTZ and PTZ.

Example 2: mAb W6/800 Binds an ERBB2 Epitope Different and Distinct from the Trastuzumab and Pertuzumab Epitopes Materials and Methods:

SK-BR-3 human breast carcinoma cells ($5 \times 10^5$) were pre-incubated on ice for 30 minutes with Phosphate (0.01 M) buffered (pH 7.4) saline (0.9%), i.e. PBS, or 50 μl of PBS containing 200 μg/ml of mAb W6/800, TTZ, or PTZ, as indicated. At the end of the pre-incubation, Fluorescein IsoThioCyanate (FITC)-labeled mAb W6/800 (10 μl, optimal pre-determined dilution) was tested for its binding ability, as indicated. An irrelevant FITC-labelled murine IgG2 antibody recognizing an epitope not expressed on breast carcinoma cells was included, as indicated. Cells were analyzed by a FACScan (B&D).

Figure 2:
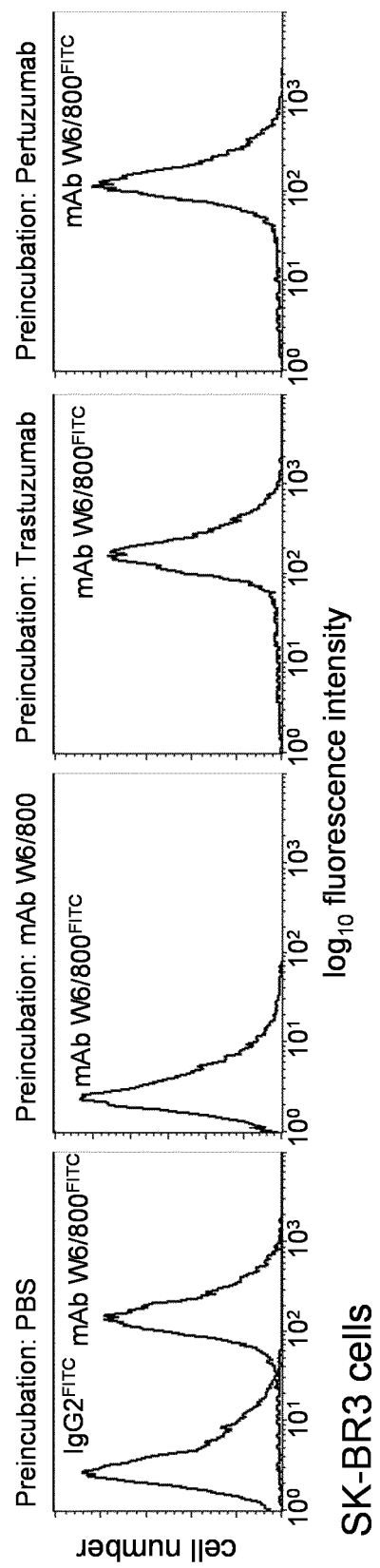
FIG. 2 shows that mAb W6/800 binds an ERBB2 ectodomain epitope different and topologically distinct from the TTZ and PTZ epitopes.

Results:

The binding of FITC-mAb W6/800 was completely blocked by pre-incubation with unlabelled mAb W6/800 (FIG. 2, second panel from left), but it was unaffected by pre-incubation with TTZ and PTZ (remaining panels). Likewise, the binding of FITC-labelled TTZ and PTZ was exclusively blocked by TTZ and PTZ, respectively, but not by mAb W6/800 (not shown). These results demonstrate that the three epitopes are different and topologically distinct.

Figure 3:
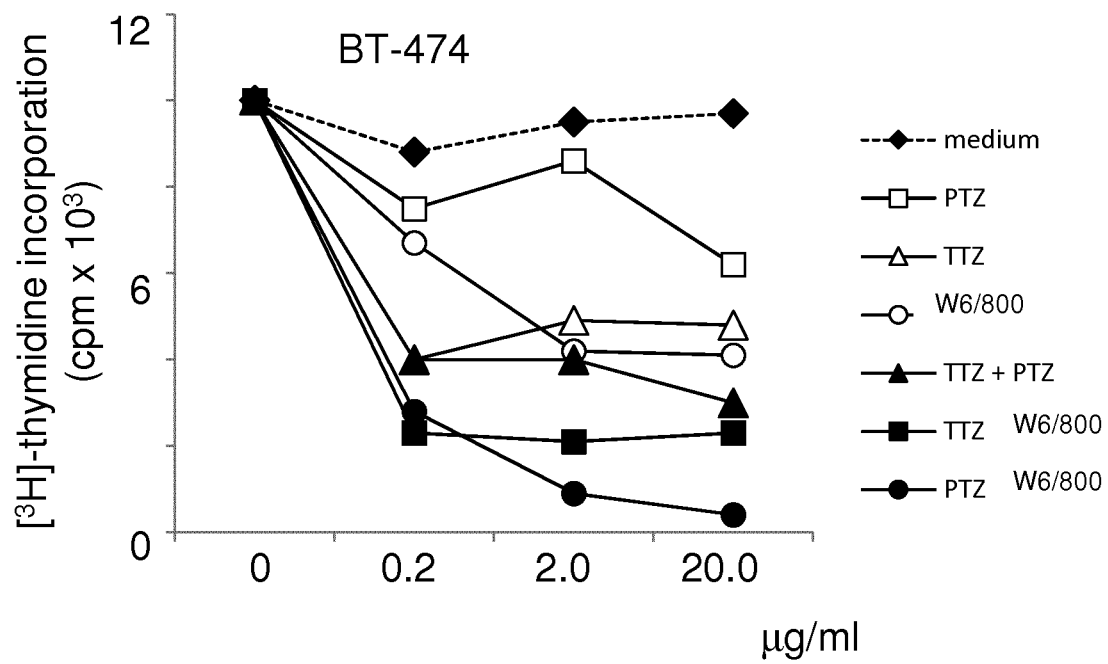
FIG. 3 shows that mAb W6/800 exerts antiproliferative effects on ERBB2-overexpressing BT-474 breast carcinoma cells. Moreover, when used in combination, mAb W6/800 synergizes with TTZ and PTZ better than they synergize with each other.

Example 3: Antiproliferative Effect of mAb W6/800 on ERBB2-Overexpressing/Amplified Cells Materials and Methods:

ERBB2-overexpressing/amplified BT-474 human breast carcinoma cells (Baselga J, et al. J Clin Oncol 2010; 28:1138-44) were grown for 18 h in RPMI 0.2% FBS. Then FBS concentration was adjusted to 10%, and the cells were grown for 48 hours in the absence and presence of escalation doses of TTZ, PTZ and mAb W6/800. In addition to single-agent treatments, the cells were also grown in the presence of the same amounts of antibodies in double-agent treatment experiments. During the last 4 h of the experiment the cells were incubated with $^3$H-Thymidine, then lysed, and TCA-precipitable counts were assessed in triplicate to determine DNA incorporation of radioactive precursors (FIG. 3).

Results:

mAb W6/800 as a single agent was similarly or more active than TTZ and PTZ. However, and surprisingly, it synergized with both more effectively than either of the two antibodies synergized with each other (FIG. 3).

Figure 4:
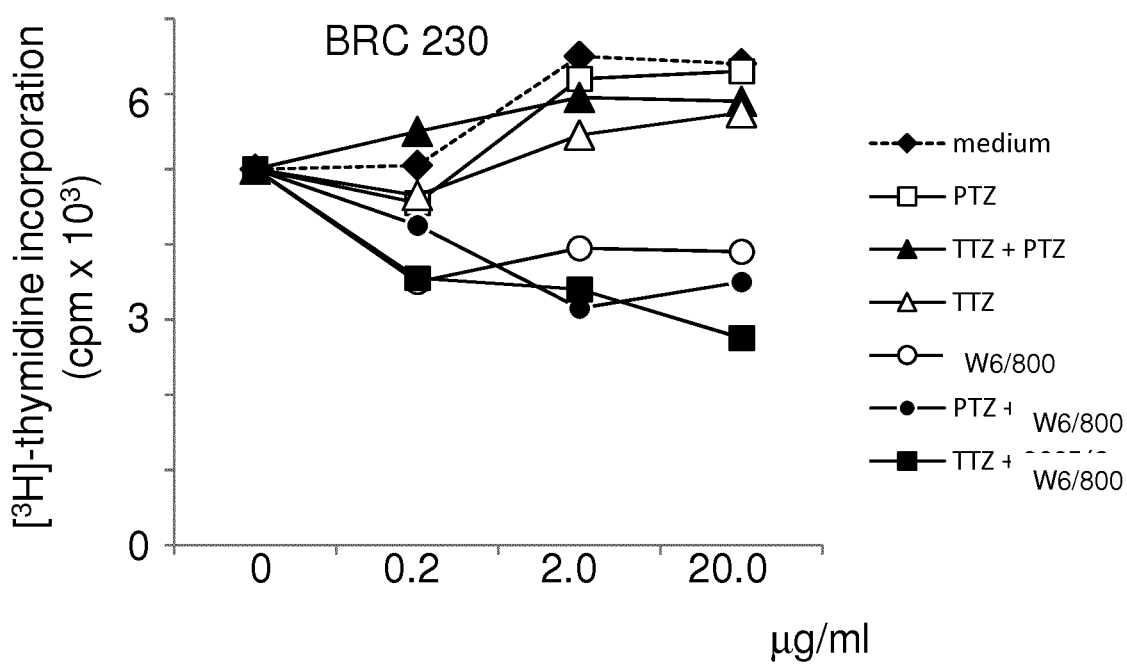
FIG. 4 shows that unlike PTZ and TTZ, mAb W6/800 has antiproliferative effects on ERBB2-low BRC230 breast carcinoma cells. In this low-ERBB2 setting, the antiproliferative effects of mAb W6/800 are additive and synergistic with those of TTZ and PTZ.

Example 4: Antiproliferative Effect of mAb W6/800 on ERBB2-Low/Non-Amplified Cells Materials and Methods:

ERBB2-low/non-amplified BRC 230 human breast cancer cells (Amadori et al. Breast Cancer Res Treat Rep 1993; 28:251-60) were grown and treated as in example 3. $^3$H-Thymidine incorporation was assessed as above (FIG. 4).

Results:

mAb W6/800 was the only effective single-agent treatment in vitro on ERBB2-low cells. In addition, it did synergize with TTZ and PTZ (FIG. 4).

Example 5: mAb W6/800 Inhibits Tumor Cell Growth In Vivo

Materials and Methods:

ERBB2-low BRC230 human breast carcinoma cells ($5 \times 10^5$) were injected subcutaneously in nu/CD1 mice (5 mice per group). When xenotransplants reached 60 mm$^3$ (time 0) mice were randomized to receive PBS, TTZ, PTZ, or mAb W6/800 by intraperitoneal injection (i.p.). Tumor growth was monitored by a caliper over the indicated times. Antibodies were administered twice a week for 3 weeks at 10 mg/kg (FIG. 5).

Figure 5:
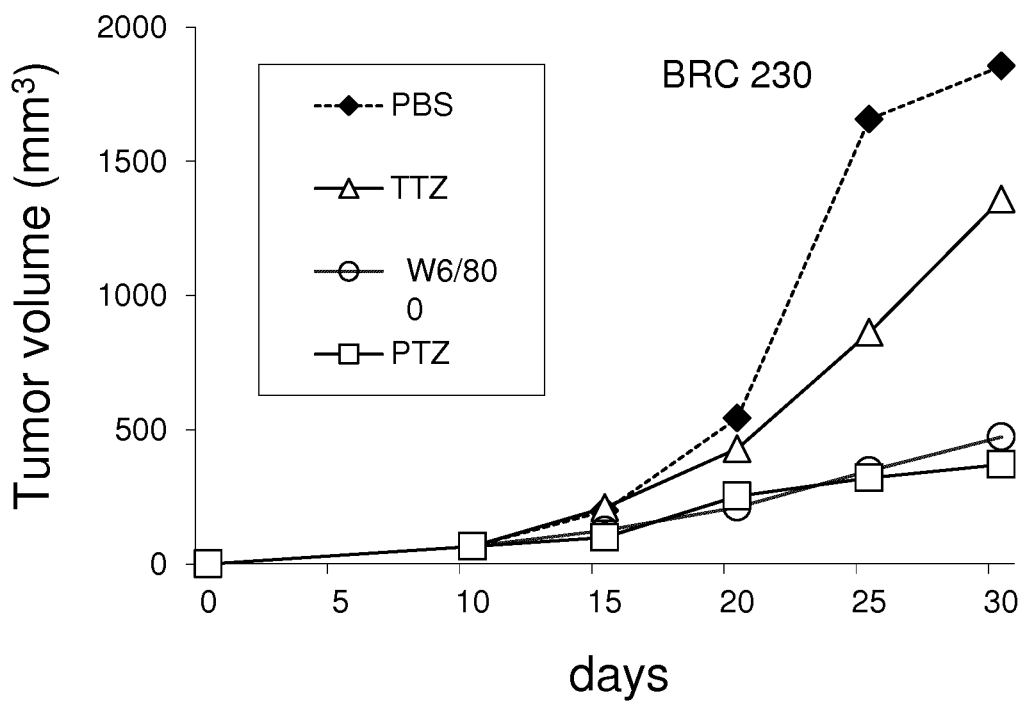
FIG. 5 shows that mAb W6/800 inhibits the growth of ERBB2-low BRC 230 tumor xenografts in nude mice better than TTZ and similar to PTZ.

Results:

mAb W6/800 was as effective as PTZ and much more effective than TTZ on tumor xenotransplants not overexpressing ERBB2 (FIG. 5).

Example 6: mAb W6/800, TTZ and PTZ Synergistically Inhibit Tumor Cell Growth In Vivo Materials and Methods:

tumor xenotransplants of ERBB2-low BRC230 human breast carcinoma cells were established and monitored (FIG. 6) exactly as described above. Treatment was carried out with the indicated antibody combinations (each mAb at 10 mg/kg).

Figure 6:
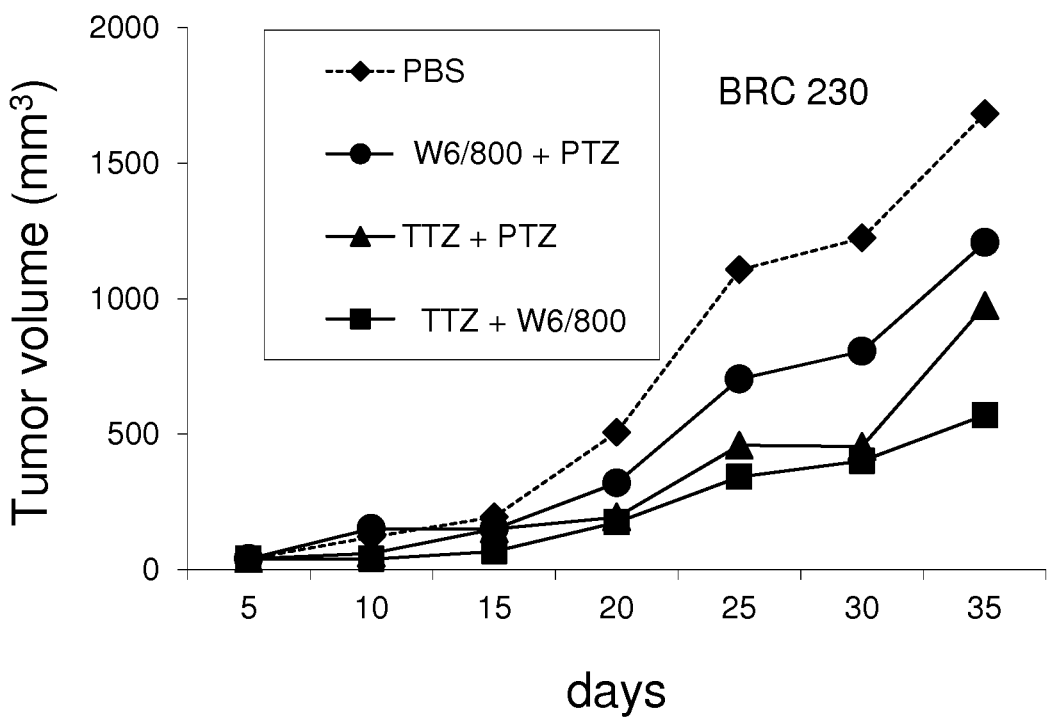
FIG. 6 shows that mAb W6/800, combined with TTZ and PTZ, inhibits the growth of ERBB2-low BRC 230 tumor xenografts in nude mice better than TTZ/PTZ combinations.

Results:

mAb W6/800-TTZ combinations were more effective than mAb W6/800-PTZ and TTZ-PTZ combinations in controlling tumor xenotransplants expressing low ERBB2 levels (FIG. 6).

Example 7

Materials and Methods:

The CDRs of the heavy and light chains of mAb W6/800 were grafted onto human Ig backbones. Humanized forms of the antibodies may be generated according to the methods known in the art such as chimerization or CDR grafting. Alternative methods for the production of humanized antibodies are well known in the art and are described in, e.g., EP-Al 0 239 400 and WO 90/07861. Human antibodies can also be derived by in vitro methods. Suitable examples include but are not limited to phage display, yeast display, and the like.

Figure 7:
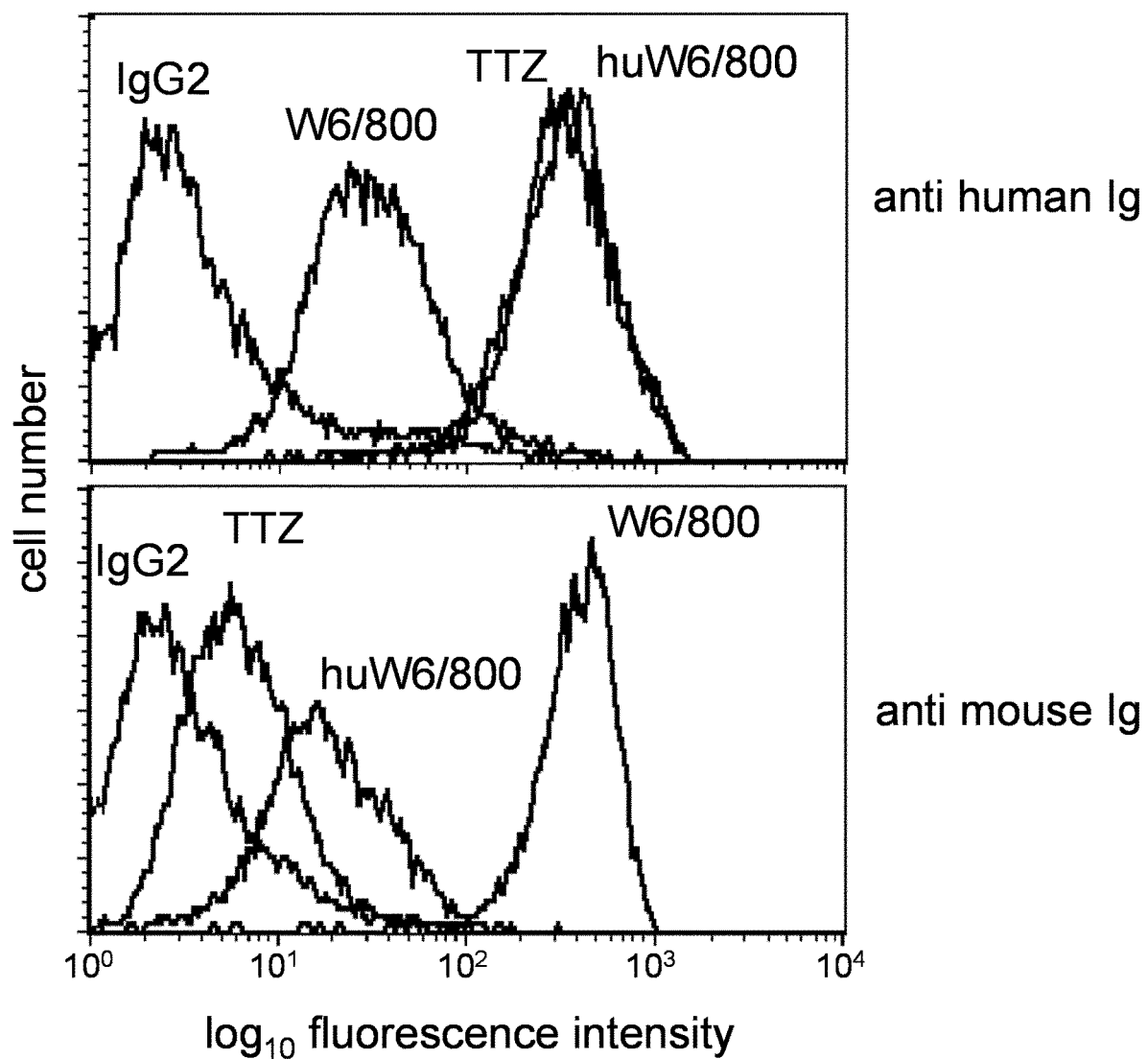
FIG. 7 shows that grafting mAb W6/800 CDRs onto a human Ig backbone results in a humanized antibody that binds breast cancer cells to an extent similar to TTZ and the parental murine mAb.

Humanized heavy SEQ NO.1 and light chains SEQ. NO.2 or SEQ. NO.3 were cloned into standard expression vectors, such as pcDNA3, or similar, and co-transfected into CHO cells. The cells were cultured in Erlenmeyer flask in incubator at 37° C., 5% $CO_2$ on a shaker at 120 rpm for at least 14 days. The surnatants were purified through standard protein A resins. The humanized W6/800 antibody huW6/800 corresponding to SEQ. NO.1 and SEQ. NO.2 purified from CHO supernatants was compared with its parental murine antibody and TTZ in its ability to bind SK-BR-3 breast carcinoma cells. Flow cytometry experiments were performed in which the three antibodies and control IgG2 of irrelevant specificity were incubated for 30 min at the same concentration (10 μg/ml), washed two times, and then revealed by incubation with FITC-labelled secondary antibodies to either human or murine Ig, as indicated (FIG. 7).

Results:

humanized antibody and TTZ displayed comparable binding to SK-BR-3 cells and substantially lost reactivity with anti murine Ig (FIG. 7), demonstrating successful grafting of W6/800 CDRs onto a human backbone. Similar results were obtained with two different antimurine Ig preparations (not shown). The humanized antibodies did not react with ERBB2-negative cells (not shown).

---

The invention claimed is:

1. An anti-ErbB2 antibody or fragment thereof comprising a Heavy chain Variable (VH) domain, said VH domain comprising Complementary Determining Regions (CDRs) having an amino acid sequence having 100% sequence identity to the amino acid sequence of the three CDRs in SEQ ID NO:1, and a Light chain Variable (VL) domain, said VL domain comprising CDRs having an amino acid sequence having 100% sequence identity to the amino acid sequence of the three CDRs in SEQ ID NO:2; said antibody or fragment thereof binding an epitope of ErbB2 receptor distinct from the epitope bound by Trastuzumab and Pertuzumab.

2. The antibody according to claim 1, which is a recombinant monoclonal antibody.

3. The antibody according to claim 1, which is humanized.

4. The antibody according to claim 1, wherein the amino acid sequence of the Heavy chain Variable (VH) domain is at least 80% identical to the amino acid sequence of SEQ ID NO:1, and wherein the amino acid sequence of the Light chain Variable (VL) domain is at least 80% identical to SEQ ID NO:2 or SEQ ID NO:3.

5. The antibody according to claim 1, wherein the antibody isotype is selected from the group consisting of an IgG1, an IgG2, an IgG3, an IgG4, an IgM, an IgA1, an IgA2, an IgA, an IgD, and an IgE antibody.

6. The antibody according to claim 1, which is coupled to a labelling group.

7. The antibody according to claim 1, which is coupled to an effector group.

8. An isolated nucleic acid encoding an antibody or antibody fragment according to claim 1.

9. A vector comprising a nucleic acid according to claim 8, which is an expression vector and the nucleic acid sequence is operably linked to a control sequence.

10. A host cell comprising the nucleic acid of claim 8 or a vector comprising said nucleic acid.

11. A pharmaceutical composition comprising:
an active ingredient selected from the group consisting of an antibody according to claim 1, a nucleic acid encoding said antibody, and a vector comprising said nucleic acid encoding said antibody; and
at least another pharmaceutically acceptable carrier, diluent and/or excipient.

12. The composition according to claim 11, further comprising another anti-neoplastic agent.

13. The composition according to claim 12 wherein the further antineoplastic agent is selected from the group consisting of gefitinib, lapatinib, sunitinib, pemetrexed, bevacizumab, cetuximab, imatinib, alemtuzumab, trastuzumab, pertuzumab, rituximab, erlotinib, and bortezomib.

14. The antibody or fragment thereof of claim 1, wherein the VH domain has an amino acid sequence having 100% sequence identity to the amino acid sequence of SEQ ID NO:1, and the VL domain has an amino acid sequence having 100% sequence identity to the amino acid sequence of SEQ ID NO:2.

15. A method for treating hyperproliferative diseases characterized by ERBB2 expression, overexpression or hyperactivity in a subject in need thereof, the method comprising:
administering to the subject a pharmaceutical composition comprising an active ingredient selected from the group consisting of an antibody according to claim 1, a nucleic acid encoding said antibody, and a vector comprising said nucleic acid encoding said antibody.

16. A method according to claim 15 wherein the hyperproliferative disease is selected from the group consisting of breast cancer, ovarian cancer, renal carcinoma, gastrointestinal/colon cancer, lung cancer, clear cell carcinoma of the kidney, prostate cancer, melanoma, and sarcoma.

17. The method according to claim 15 wherein the active ingredient is administered in combination with at least one further antineoplastic agent.

18. The method according to claim 17 where in the further antineoplastic agent is selected from the group consisting of gefitinib, lapatinib, sunitinib, pemetrexed, bevacizumab, cetuximab, imatinib, alemtuzumab, trastuzumab, pertuzumab, rituximab, erlotinib, and bortezomib.

19. A method of diagnosing a cancer associated with ERBB2 in a subject, comprising:
   (a) contacting, ex vivo or in vivo, cells from the subject with the antibody or fragment thereof according to claim 1 and
   (b) measuring said antibody or fragment thereof binding to ERBB2 on the cells from the subject, wherein a higher level of antibody binding to ERBB2 on the cells from the subject compared to cells of a subject not having cancer indicate that the subject has a cancer associated with ERBB2.

* * * * *

SEQUENCE LISTING

```
<160> NUMBER OF SEQ ID NOS: 5

<210> SEQ ID NO 1
<211> LENGTH: 120
<212> TYPE: PRT
<213> ORGANISM: artificial
<220> FEATURE:
<223> OTHER INFORMATION: VH domain humized mAB w6/800
<220> FEATURE:
<221> NAME/KEY: DOMAIN
<222> LOCATION: (26)..(36)
<223> OTHER INFORMATION: CDR1
<220> FEATURE:
<221> NAME/KEY: DOMAIN
<222> LOCATION: (50)..(65)
<223> OTHER INFORMATION: CDR2
<220> FEATURE:
<221> NAME/KEY: DOMAIN
<222> LOCATION: (96)..(109)
<223> OTHER INFORMATION: CDR3

<400> SEQUENCE: 1

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Ser Asn Tyr
            20                  25                  30

Trp Ile Glu Trp Val Arg Gln Ala Pro Gly Gln Gly Leu Glu Trp Met
        35                  40                  45
```

```
Gly Glu Ile Leu Pro Gly Ser Gly Ser Thr Asn Tyr Asn Glu Lys Leu
            50                  55                  60

Lys Gly Arg Val Thr Ser Thr Arg Asp Thr Ser Ile Ser Thr Ala Tyr
 65                  70                  75                  80

Met Glu Leu Ser Arg Leu Arg Ser Asp Asp Thr Gly Val Tyr Tyr Cys
                85                  90                  95

Ala Arg Gly Gly Gly Asn Tyr Pro Tyr Tyr Phe Asp Tyr Trp Gly Gln
               100                 105                 110

Gly Thr Thr Val Thr Val Ser Ser
               115                 120

<210> SEQ ID NO 2
<211> LENGTH: 106
<212> TYPE: PRT
<213> ORGANISM: artificial
<220> FEATURE:
<223> OTHER INFORMATION: VL domain humanized mAb w6/800
<220> FEATURE:
<221> NAME/KEY: DOMAIN
<222> LOCATION: (21)..(34)
<223> OTHER INFORMATION: CDR1
<220> FEATURE:
<221> NAME/KEY: DOMAIN
<222> LOCATION: (50)..(59)
<223> OTHER INFORMATION: CDR2
<220> FEATURE:
<221> NAME/KEY: DOMAIN
<222> LOCATION: (85)..(100)
<223> OTHER INFORMATION: CDR3

<400> SEQUENCE: 2

Asp Ile Gln Met Thr Gln Ser Pro Ser Thr Leu Ser Ala Ser Val Gly
 1               5                  10                  15

Asp Arg Val Thr Ile Thr Cys Lys Ala Ser Gln Asp Val Gly Thr Ala
                20                  25                  30

Val Ala Trp Tyr Gln Gln Lys Pro Gly Lys Ala Pro Lys Leu Leu Ile
                35                  40                  45

Tyr Trp Ala Ser Thr Arg His Thr Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Asp Tyr Phe Cys Gln Gln Tyr Ser Ser Tyr Arg Thr
                85                  90                  95

Phe Gly Ala Gly Thr Lys Leu Glu Ile Lys
               100                 105

<210> SEQ ID NO 3
<211> LENGTH: 106
<212> TYPE: PRT
<213> ORGANISM: artificial
<220> FEATURE:
<223> OTHER INFORMATION: VL domain humanized mAb w6/800
<220> FEATURE:
<221> NAME/KEY: DOMAIN
<222> LOCATION: (21)..(34)
<223> OTHER INFORMATION: CDR1
<220> FEATURE:
<221> NAME/KEY: DOMAIN
<222> LOCATION: (50)..(59)
<223> OTHER INFORMATION: CDR2
<220> FEATURE:
<221> NAME/KEY: DOMAIN
<222> LOCATION: (85)..(100)
<223> OTHER INFORMATION: CDR3
```

-continued

<400> SEQUENCE: 3

Ala Ile Gln Leu Thr Gln Ser Pro Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Phe Cys Gln Gln Tyr Ser Ser Tyr Arg Thr
                85                  90                  95

Phe Gly Ala Gly Thr Lys Leu Glu Ile Lys
            100                 105

<210> SEQ ID NO 4
<211> LENGTH: 120
<212> TYPE: PRT
<213> ORGANISM: artificial
<220> FEATURE:
<223> OTHER INFORMATION: VH domain murine mAB w6/800
<220> FEATURE:
<221> NAME/KEY: DOMAIN
<222> LOCATION: (26)..(36)
<223> OTHER INFORMATION: CDR1
<220> FEATURE:
<221> NAME/KEY: DOMAIN
<222> LOCATION: (50)..(65)
<223> OTHER INFORMATION: CDR2
<220> FEATURE:
<221> NAME/KEY: DOMAIN
<222> LOCATION: (96)..(109)
<223> OTHER INFORMATION: CDR3

<400> SEQUENCE: 4

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Asn Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Leu
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Gly Val Tyr Tyr Cys
                85                  90                  95

Ala Arg Gly Gly Gly Asn Tyr Pro Tyr Tyr Phe Asp Tyr Trp Gly Gln
            100                 105                 110

Gly Thr Thr Val Thr Val Ser Ser
        115                 120

<210> SEQ ID NO 5
<211> LENGTH: 104
<212> TYPE: PRT
<213> ORGANISM: artificial
<220> FEATURE:
<223> OTHER INFORMATION: VL domain murine mAB w6/800
<220> FEATURE:
<221> NAME/KEY: DOMAIN
<222> LOCATION: (21)..(34)

```
<223> OTHER INFORMATION: CDR1
<220> FEATURE:
<221> NAME/KEY: DOMAIN
<222> LOCATION: (50)..(59)
<223> OTHER INFORMATION: CDR2
<220> FEATURE:
<221> NAME/KEY: DOMAIN
<222> LOCATION: (85)..(100)
<223> OTHER INFORMATION: CDR3

<400> SEQUENCE: 5

Ile Glu Leu Met Thr Gln Ser His Lys Phe Met Ser Thr Ser Val Gly
 1               5                  10                  15

Asp Arg Val Ser Ile Thr Cys Lys Ala Ser Gln Asp Val Gly Thr Ala
             20                  25                  30

Val Ala Trp Tyr Gln Gln Lys Pro Gly Gln Ser Pro Lys Leu Leu Ile
         35                  40                  45

Tyr Trp Ala Ser Thr Arg His Thr Gly Val Pro Asp Arg Phe Thr Gly
     50                  55                  60

Ser Gly Ser Gly Thr Asp Phe Thr Leu Thr Ile Ser Asn Val Gln Ser
 65                  70                  75                  80

Glu Asp Leu Ala Asp Tyr Phe Cys Gln Gln Tyr Ser Ser Tyr Arg Thr
                 85                  90                  95

Phe Gly Ala Gly Thr Lys Leu Glu
                100
```